United States Patent [19]

Albin et al.

[11] Patent Number: 4,909,069

[45] Date of Patent: Mar. 20, 1990

[54] METHOD AND APPARATUS FOR DETECTING LEAKS IN RUBBER GLOVES AND THE LIKE

[75] Inventors: Maurice S. Albin; Leonid Bunegin, both of San Antonio, Tex.

[73] Assignee: Utah Medical Products, Inc., Midvale, Utah

[21] Appl. No.: 379,721

[22] Filed: Jul. 14, 1989

Related U.S. Application Data

[63] Continuation of Ser. No. 126,001, Nov. 27, 1987, abandoned.

[51] Int. Cl.$^4$ .......................... A61B 19/00; G01M 3/40
[52] U.S. Cl. ........................................ 73/40; 340/605; 324/557
[58] Field of Search ................... 73/40; 324/557, 558, 324/559; 340/604, 605, 573; 128/303.13, 303.14, 382, 419 R; 361/224

[56] References Cited

U.S. PATENT DOCUMENTS

| | | | |
|---|---|---|---|
| 2,981,886 | 4/1961 | Beck | 324/557 |
| 3,414,848 | 12/1968 | Thomas | 324/557 |
| 3,758,855 | 9/1973 | Meyer | 340/604 |
| 3,935,567 | 1/1976 | Reynolds | 73/40.5 R |
| 4,047,424 | 9/1977 | Rollason et al. | 73/52 |
| 4,110,739 | 8/1978 | Kidd | 340/604 |
| 4,205,672 | 6/1980 | Dvorak | 128/138 |
| 4,268,824 | 5/1981 | Phillips | 340/604 |
| 4,321,925 | 3/1982 | Hoborn et al. | 361/224 |
| 4,558,309 | 12/1985 | Antonevich | 340/649 |
| 4,583,039 | 4/1986 | Kolcio et al. | 324/557 |
| 4,602,773 | 7/1986 | Craven, Jr. | 604/356 |
| 4,650,477 | 3/1987 | Johnson | 604/118 |
| 4,692,748 | 9/1987 | Pinsak et al. | 340/573 |

FOREIGN PATENT DOCUMENTS

| | | | |
|---|---|---|---|
| 2208300 | 6/1974 | France | |
| 203949 | 11/1984 | Japan | 340/604 |

OTHER PUBLICATIONS

Beck, "Holes in Rubber Gloves Description of a New Instrument to Detect Holes During Operations," 29, *Guthrie Clin. Bull.*, 14–18, (1959).
Beck, "Holes in Rubber Gloves," 100(3), *The American Journal of Surgery*, 363–364, (Sep. 1960).
Sabiston, Jr., *Davis–Christopher Textbook of Surgery: The Biological Basis of Modern Surgical Practice*, W. B. Saunders Company, 11th Ed., 328–338, (1977).
McCue et al., "Efficacy of Double-Gloving as a Barrier to Microbial Contamination During Total Joint Arthroplasty," *The Journal of Bone and Joint Surgery*, 811–813, (1981).
Freeman et al., "Use of Gloves among Dermatologists," 17(2)(1), *Journal of the American Academy of Dermatology*, 320–323, (Aug. 1987).
Cole et al., "Inadequacies of Present Methods of Surgical Skin Preparation," 89, Archives of Surgery, 215, (1964).

*Primary Examiner*—Hezron E. Williams
*Attorney, Agent, or Firm*—Woodard, Emhardt, Naughton, Moriarty & McNett

[57] ABSTRACT

Method and apparatus for detecting leaks in a rubber glove or the like. The wearer of rubber gloves connects a clip to his ear and places each glove-covered hand individually into electrolyte liquid in an electrically conductive receptacle. A circuit including a buzzer or beeper sounds if there is a leak in the glove. The circuit includes a clip connected to the wearer's ear as well as the beeper, the electrolyte, a battery and the receptacle. An alternative embodiment includes a removable disposable electrically non-conductive receptacle for the electrolyte liquid with the circuit including an electrical conductor cemented to the inside of the receptacle and in the circuit.

3 Claims, 1 Drawing Sheet

METHOD AND APPARATUS FOR DETECTING LEAKS IN RUBBER GLOVES AND THE LIKE

This application is a continuation of application Ser. No. 126,001, now abandoned, filed Nov. 27, 1987.

BACKGROUND OF THE INVENTION

This invention refers to leak detectors for detecting leaks in rubber gloves and the like.

Many persons are employed in positions where the hands could be at risk for infections and contamination by hazardous biological or chemical products. To prevent contact with such hazardous materials, manufacturers have developed rubber or plastic gloves impermeable to such materials. However, imperfections in the manufacturing process or heavy use and wear and tear often leads to the development of both visible and non-visible leaks in such gloves. Visible inspection of such gloves can be both inaccurate and time consuming, particularly where the leak is small or non-visible, or in a relatively inaccessible location. Consequently, there is a need for a fast, accurate method and means for detecting leaks in rubber gloves.

Various devices for sensing leaks or continuity are known in the art. Thus the Reynolds U.S. Pat. No. 3,935,567 discloses a device for detecting leaks in a gasoline dispensing operation. The device includes a pressure sensitive switch, a timing circuit and an indicator means. The Kidd U.S. Pat. No. 4,110,739 discloses a means for detecting leakage in the inner lining of tanks and piping. The means includes a probe, an alarm and a power source. When the leak occurs, a circuit is made sounding the alarm. The Rollason et al. U.S. Pat. No. 4,047,424 relates to apparatus for non-destructive leak testing of primary electrochemical cells. The apparatus includes containers which receive the cells in deionized water. A probe and a meter are provided to measure conductivity of the water after the cell has been in the water a predetermined period of time.

A device for testing the continuity of a circuit is disclosed in U.S. Pat. No. 4,558,309 to Antonevich. The device includes a grounding of the human body to prevent static build up. An alarm is sounded when an open circuit is detected between the human body and ground. The U.S. Pat. No. 4,692,748 to Pinsak discloses a glove apparatus for deterring thumbsucking wherein an electrical circuit is made through the human body when the glove on the thumb is placed in the mouth. The Dvorak U.S. Pat. No. 4,205,672 discloses a conductivity sensing device for diapers. When the sensing device is connected, the diaper is a part of a circuit which includes an LED. The LED blinks when the diaper is wet and the circuit is closed.

SUMMARY OF THE INVENTION

One embodiment of the apparatus of the present invention might include apparatus for detecting a leak in a rubber glove or the like worn by a subject. There is provided a vessel containing an electrolyte. Also provided is means for electrically detecting a leak in the glove worn by the subject and placed in the electrolyte. The detecting means includes circuit means for detecting closure of an electrical circuit between the subject and the electrolyte through the leak.

One embodiment of the method for detecting a leak in a rubber glove of the present invention might include putting the glove on the hand of a person and then connecting an electrical circuit to the body of the person with the electrical circuit including a vessel containing electrolyte. Next, the gloved hand of the person is dipped into the vessel and electrolyte to actuate a signal in response to closure of an electrical circuit between the person and the electrolyte through the leak.

It is an object of this invention to provide a leak detector for rubber gloves.

Another object of the present invention is to provide apparatus operable to detect both visible and non-visible leaks in gloves constructed of rubber or plastic or some other membrane material.

Further objects of the invention will appear as the description proceeds.

DESCRIPTION OF THE PREFERRED EMBODIMENT

For the purpose of promoting an understanding of the principles of the invention, reference will now be made to the embodiment illustrated in the accompanying drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
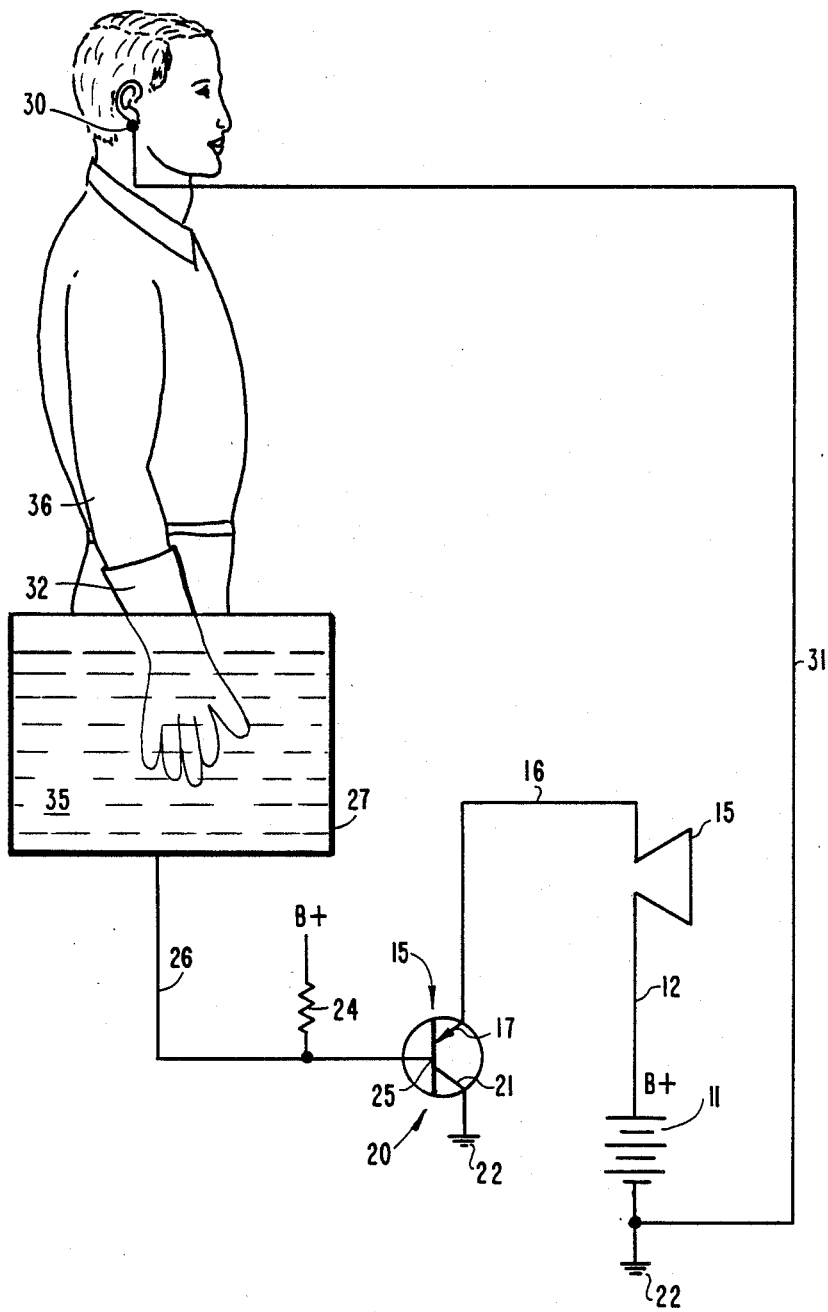
FIG. 1 is a schematic drawing of the present invention.

Referring now more particularly to FIG. 1, there is shown a battery 11 electrically connected by an insulated electrical wire lead 12 to a buzzer or beeper 15, which is electrically connected by insulated wire lead 16 to the emitter 17 of a switching transistor 20. The collector 21 of the switching transistor is electrically connected to electrical ground 22. The switching transistor 20 is designed such that in order for electrically current to flow from the emitter side of the transistor to the collector side, its base must be brought to electrical ground. The base 25 of the switching transistor is electrically connected by insulated electrical wire lead 26 to a vessel 27 constructed of electrically conductive material, such as a large, stainless steel bowl. The base is also connected through resistor 24 to a source of B+ voltage which in this case is the positive terminal of the battery. The vessel 27 contains a volume of electrolyte 35, such as a 0.9% saline solution. In one embodiment of the invention, the switching transistor 20 is a Texas Instruments 2N3962, the battery 11 is an Eveready 216 9-volt battery, and the buzzer 15 is, in fact, a beeper, Murata brand, of the type found in a watch or in a personal belt-carried telephone signalling device. An electrically conductive clip 30, constructed such that it clings comfortably to an earlobe, is electrically connected by insulated electrical wire lead 31 to electrical ground 22. Such a clip is commercially available from the Grass Instrument Company.

In order to use the testing device, the person who is going to use the rubber gloves puts them on. He then dips his glove-covered hands, one at a time, into the electrolyte. When a leak exists in a glove 32 to be tested for leaks, the electrolyte 35 comes into contact with the human body 36 through the leak, and an electrical circuit is completed from the base 25 of the switching transistor 20 through the insulated electrical wire lead 26, through the electrically conductive vessel 27, through the electrolyte 35, through the body 36, through the electrically conductive clip 30, through the insulated electrical wire lead 31, to electrical ground 22, thus bringing the base of the switching transistor 20 to electrical ground. When the base of the switching transistor 20 is brought to ground, transistor 20 closes the circuit and permits electrical current from battery 11 to flow through beeper 15, activating the same, and informing the individual that the glove has a leak.

Figure 2:
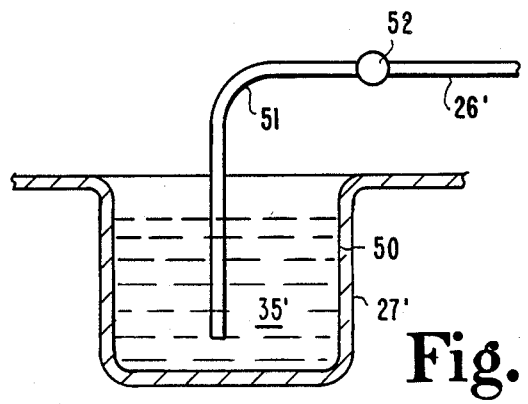
FIG. 2 is a schematic drawing of an alternative embodiment of the invention.

Referring to FIG. 2, an alternative embodiment of the invention includes using a removable non-electrically conductive liner 50 inside of the vessel 27' with an electrical conductor 51 cemented to the liner. The lead 26' is connected to the electrical conductor in use. The advantage of using the removable liner is that it can be disposed of after the sterile electrolyte 35' becomes contaminated. This, of course, occurs or may occur when a leak is discovered in a glove or even may occur when a test is performed showing no leak, if the external surface of the glove has been contaminated prior to the test. After such contamination, the electrolyte and removable liner may be disposed of and replaced. The embodiment of FIG. 2 is otherwise identical to that of FIG. 1.

One specific example of the use of the disposable removable liner might be in the surgical operating room. The surgeon scrubs and puts on the sterile gown and gloves. As soon as the gloves are on, he uses the present apparatus to test for leaks. If there is a leak, the gloves can be discarded and the electrolyte and removable liner disposed of. Also during the surgical procedure, at appropriate breaks in the surgical procedure, the gloves can be rechecked and the gloves and removable liner and electrolyte disposed of and replaced, if necessary.

It should be understood that the above-described embodiment can be varied in various ways within the scope of the invention. For example, it is required by AAMI standards that only a certain amount of current should flow through the human body. It is presently believed this amount is on the order of 10 $\mu A$. The abovedescribed circuit may be modified to provide additional resistance in series with the lead 26 or 26' if necessary to meet such standards.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method for detecting leaks in rubber gloves during a single medical procedure, comprising the steps of:

putting the glove on the hand of a person;

connecting an electrical circuit to the body of the person with the electrical circuit including an electrical conductor, wherein said electrical conductor is in electrical communication with a solution of electrolyte contained in a vessel with a removable and replaceable liner interposed between said solution of electrolyte and said vessel;

dipping the gloved hand of the person in the vessel and electrolyte to actuate a signal in response to closure of an electrical circuit between the person and the electrolyte through the leak;

providing a plurality of sterile removable and replaceable liners; and, removing and replacing said liner and said solution with a sterile liner and a new solution of electrolyte upon actuation of the signal.

2. The method for detecting leaks in rubber gloves during a single medical procedure of claim 1 wherein said connecting step includes said electrical circuit including a wire lead and wherein said conductor is fixedly connected at one end to said liner and removably connectable at an opposite end to said wire lead.

3. An apparatus for detecting a leak in a protective glove worn by a subject, comprising:

a vessel;

a disposable liner removably inserted within said vessel, said liner containing an electrolyte;

detecting means for electrically detecting a leak in the glove worn by the subject and placed in said electrolyte, said detecting means being electrically connected to said electrolyte and including circuit means for detecting closure of an electrical circuit between the subject and said electrolyte through the leak;

wherein said detecting means includes an electrical conductor removably connected to a wire lead which leads to said circuit means, wherein said electrical conductor is affixed to said liner and disposable with said liner, and wherein, after disposal of said liner and conductor, a new disposable liner and conductor may be provided with said new electrical conductor being removably connected to said lead.

* * * * *